(12) United States Patent  
Barbera-Guillem et al.

(10) Patent No.: US 6,555,365 B2  
(45) Date of Patent: Apr. 29, 2003

(54) MICROINCUBATOR COMPRISING A CELL CULTURE APPARATUS AND A TRANSPARENT HEATER

(75) Inventors: Emilio Barbera-Guillem, Powell; Rick D. Lucas, Galena, both of OH (US)

(73) Assignee: BioCrystal, Ltd., Westerville, OH (US)

( * ) Notice: Subject to any disclaimer, the term of this patent is extended or adjusted under 35 U.S.C. 154(b) by 0 days.

(21) Appl. No.: 09/732,162

(22) Filed: Dec. 7, 2000

(65) Prior Publication Data

US 2002/0072113 A1 Jun. 13, 2002

(51) Int. Cl.[7] ................................................ C12M 1/00
(52) U.S. Cl. ................. 435/303.1; 435/297.1; 435/305.3; 219/544; 219/548
(58) Field of Search .......................... 435/297.1, 304.1, 435/305.3, 303.1; 219/522, 544, 548; 359/512

(56) References Cited

U.S. PATENT DOCUMENTS

| | | | | |
|---|---|---|---|---|
| 5,565,353 A | | 10/1996 | Klebe et al. ................. 435/383 |
| 5,717,190 A | * | 2/1998 | Inoue .......................... 219/522 |
| 5,973,301 A | * | 10/1999 | Inoue .......................... 219/522 |
| 6,008,010 A | | 12/1999 | Greenberger et al. ......... 435/41 |

* cited by examiner

*Primary Examiner*—David A. Redding  
(74) *Attorney, Agent, or Firm*—M. Bud Nelson

(57) ABSTRACT

Provided for heating cultured cells is a controlled heater device comprising a cell culture apparatus, a transparent heater in thermal contact with the cell culture apparatus, and may further comprise one or more of a transparent filter provided to prevent a predetermined spectral range of light from passing through the transparent filter, and a power source for controlling the amount of heat generated by the transparent heater of the controlled heater device.

27 Claims, 3 Drawing Sheets

MICROINCUBATOR COMPRISING A CELL CULTURE APPARATUS AND A TRANSPARENT HEATER

FIELD OF THE INVENTION

The present invention relates to generally to the field of cell culture; and more particularly to a system that enables the observation and characterization of cultured cells, outside the environment of a cell culture incubator, over a desired period of time.

BACKGROUND OF THE INVENTION

Genomics, proteomics, and drug discovery are generating a need for expanded versatility of applications for manipulating cell cultures, as well as a greater need for efficient and economical growth of cultured cells in high volume. For example, in developing and testing potential therapeutic agents (e.g., including, but not limited to, genetic vectors, genetic sequences, vaccines, drugs, growth factors, cytokines, and the like), it may often be desirable to visually characterize the response to cells after treatment with the therapeutic agent. Additionally, it may be desirable to visually evaluate the response of treated cells to various stimuli such as physical, chemical or environmental (e.g., temperature) stress. Typical cell response parameters include, but are not limited to, cell migration, cell adhesion, cell outgrowth (e.g., neurite outgrowth rate), cell division, induction of apoptosis, induction of molecule production (e.g., visible if labeled with a detectable label), and molecule movement (e.g., such as labeled by a fluorescent protein) during discrete stages of the cell cycle. As apparent to one skilled in the art, there are additional technologies (e.g., in vitro fertilization, and in vitro cloning) that could be advanced with better means for visualizing cellular interactions between cells in culture.

However, traditional cell culture devices and methods do not provide a simple, cost effective solution for applications related to visualization and characterization of cell growth, differentiation, or interactions in vitro. For example, while time-lapse videorecording is suitable for observation of individual cells at high magnification, traditional time-lapse image analyzers are both complex and costly. Additionally, maintaining a cell culture in traditional cell culture devices for visually observing response parameters requires that the cell culture device be placed in a controlled environment (e.g., conventional tissue culture incubator, or continual infusion of gases such as oxygen or carbon dioxide and/or of fresh tissue culture medium).

Thus, there is a need for a cell culture system which provides: optimal gas transfer for a desired time period independently of instrumentation for supplying such gases (e.g., one or more of a traditional cell culture incubator, and a $CO_2$ tank for supplying $CO_2$ or a $CO_2/N_2$ mix); is adapted for achieving uniform heating of an individual cell culture; and enables visual observation of response parameters in a simple, cost-effective manner.

SUMMARY OF THE INVENTION

It is a primary object of the invention to maintain a desired temperature of cells cultured in a cell culture apparatus without the need of a traditional cell culture incubator.

It is another object of the invention to provide a controlled heater device that is adapted to uniformly heat cells cultured in the controlled heater device.

It is another object of the present invention to provide a controlled heater device that is adapted to uniformly heat cultured cells, and that enables visual observation of cell response parameters in a simple, cost-effective manner.

It is another object of the present invention to provide a controlled heater device that is adapted to uniformly heat cultured cells, that enables visual observation of cell response parameters in a simple, cost-effective manner, and that provides optimal gas transfer for a desired time period and independently of instrumentation for supplying such gases.

It is another object of the present invention to provide a controlled heater device that is adapted to uniformly heat cultured cells, and that enables observation of cell response parameters by image analysis, such as by time-lapse videorecording.

Briefly, the invention provides for a controlled heater device, adapted to uniformly heat cultured cells, comprising a cell culture apparatus which provides optimal gas transfer through one or more of its surfaces, a transparent heater for heating cells cultured in the cell culture apparatus at a desired temperature; and may further comprise a power source for controlling the temperature of the controlled heater device, a transparent filter adapted to pass light of desired wavelengths therethrough, and a combination thereof. Preferably, the controlled heater device, because of alignment between its transparent components, provides an optical path that enables imaging of cells cultured in the controlled heater device (e.g., when imaged through a microscope).

These and other objects and advantages of the invention will become more apparent from the following detailed description taken in conjunction with the accompanying drawings.

DETAILED DESCRIPTION OF THE INVENTION

Definitions

The term "transparent" is used herein, for purposes of the specification and claims and with respect to a surface of the cell culture apparatus, with respect to the heater and with respect to a pressure-sensitive adhesive, to mean that light transmission is 70% or more, and more preferably 90% or more, in a visible light range. The term "transparent" is used herein, for purposes of the specification and claims and with respect to a filter in the device according to the present invention, to mean that light transmission is 70% or more, and more preferably 90% or more, of a predetermined spectral range of light.

Figure 1:
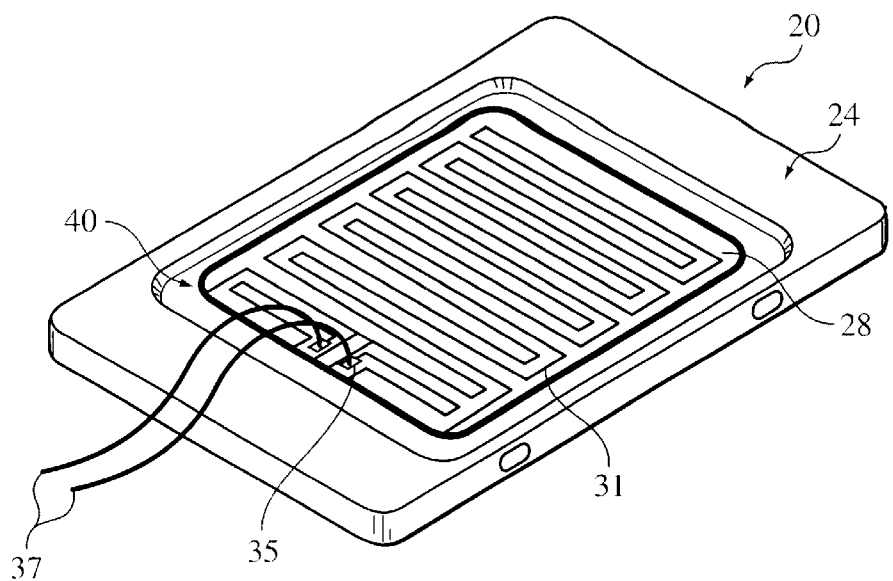
FIG. 1 is a perspective view of an embodiment of the controlled heater device according to the present invention.

Referring to FIG. 1, controlled heater device 20, adapted to uniformly heat cultured cells, comprises cell culture apparatus 24 which provides optimal gas transfer through one or more of its surfaces, and at least one transparent heater 28 in thermal contact with cell culture apparatus 24. It will be apparent to one skilled in the art that cells which can be cultured in the controlled heater device may comprise one or more cell types includeing, but not limited to, animal cells, insect cells, mammalian cells, human cells, transgenic cells, genetically engineered cells, transformed cells, cell lines, plant cells, anchorage-dependent cells, anchorage-independent cells, and other eukaryotic cells.

Cell culture apparatus 24 is described in more detail in co-pending U.S. application Ser. No. 09/526,006, and continuing applications (the disclosures of which are herein incorporated by reference). Briefly, the cell culture apparatus is comprised of a frame to which is contacted and secured taut thereto, in a leak-proof sealing arrangement, at least one gas permeable, liquid impermeable membrane. In a preferred embodiment, two liquid impermeable membranes are secured thereto, wherein at least one of the membranes is gas-permeable; and more preferably, both membranes are gas permeable. The frame may be of a basic biocompatible composition that may comprise suitable plastic, thermoplastic, synthetic, or natural materials which can be fabricated into a framework structure, thereby achieving the required structural integrity for its intended purpose. In a further embodiment, the frame further comprises an identification code. An identification code comprises an identifier placed on or made a part of a frame, and which may include, but is not limited to, a bar code, a number, a series of numbers, a color, a series of colors, a letter, a series of letters, a symbol, a series of symbols, and a combination thereof. The identification code may be used for one or more of tracking, locating, identifying, identifying the position of (e.g., as relative to a point of origin), and cataloging the cell culture apparatus having that identification code which is sought to be identified. While the identification code can be placed anywhere on the frame, preferably the identification code is placed on an edge of the frame. The culture chamber of the cell culture apparatus, such as formed by the frame and two membranes, is accessed by at least one access port which extends between the outer surface of the frame and the chamber. The at least one access port is resealable, and serves as a means by which substances (e.g., cells in a fluid and/or tissue culture growth medium) can be introduced into, or withdrawn from, the chamber which is maintained as sterile. In a preferred embodiment, the at least one access port is sealed by a septum which comprises an elastomeric material that fills all or a substantial portion of the access port, and which is sufficiently pliable to be self-sealing; e.g., thereby allowing for penetration by a tip, and resealing after tip withdrawal. The elastomeric material may be natural or synthetic and may be a material including, but not limited to, silicone rubber, fluorocarbon rubber, butyl rubber, polychloroprene rubber, a silicone elastomer composite material, thermoplastic elastomer, medical grades of silicone rubber, polyisoprene, a synthetic isoprene, and a combination thereof. The elastomeric material may be selected to have a Shore A durometer within the range of from about 30 to about 80, and may further comprise an antimicrobial agent (e.g., triclosan or 5-chloro-2-(2,4-dichloro-phenoxy)phenol) incorporated therein and forms a surface coating on the septum. Preferably, the antimicrobial agent exhibits migration through the elastomeric material as the surface coating of antimicrobial agent is depleted. The gas permeable membrane is capable of allowing transfer of gases into and out of the culture chamber, and preferably is optically transparent and clear for permitting observation of the cell culture. In general, the thickness of the gas permeable membrane can range from less than about 0.00125 inches to about 0.005 inches, and more preferably in the range of about 0.002 inches to about 0.004 inches. The gas permeable membrane may be comprised of a suitable polymer that may include, but is not limited to, polystyrene, polyethylene, polycarbonate, polyolefin, ethylene vinyl acetate, polypropylene, polysulfone, poly-tetrafluoroethylene, or a silicone copolymer. In a more preferred embodiment, the gas permeable membrane has been treated, on a side of the membrane which may serve as a surface for attachment of anchorage-dependent cells in culture, by ionization to improve adhesion of the treated membrane surface to anchorage-dependent cells. Ionization of the membrane may render the treated membrane surface more hydrophilic, and can be performed using methods known in the art which include plasma discharge, corona discharge, gas plasma discharge, ion bombardment, ionizing radiation, and high intensity UV light. In a preferred embodiment, the gas permeable membrane is comprised of polystyrene or polypropylene, is treated on at least one side by corona treatment, and is about 0.004 inches thick. The at least one gas permeable membrane may be secured to frame 18 in a leak-proof sealing using means that may include mechanical means, chemical means (an adhesive agent which may include, but is not limited to, a pressure-sensitive acrylic adhesive, hot-melt adhesive, rubber cement, or any other form of adhesive or bonding agent useful for the purposes attendant to the present invention), or other suitable means. Other suitable means may include one or more of heat bonding, sonic welding, pressure fit sealing in forming a leak-proof seal, and a molding process in which the one or more membranes become an integral part of the frame (e.g., by extrusion). The cell culture apparatus provides an unexpected combination of properties including gas exchange and equilibrium, oxygenation of cells cultured in the apparatus along an attachment surface which promotes even distribution of anchorage dependent cells, spatial efficiency, versatility, and conditions which can promote a high rate of cell growth in achieving a high cell density in a relatively short period of time as compared to conventional cell culture devices. In a preferred embodiment, the cell culture apparatus is of a general shape and size to be accommodated by and held in position in a standard mechanical stage specimen holder of a microscope. In a more preferred embodiment, the cell culture device has a length in a range of from about 10 cm to about 13.5 cm, a width in a range of from about 7 cm to about 9 cm, and a height in a range of from about 0.2 cm to about 1.0 cm. In a most preferred embodiment, the cell culture device has a length of about 12.7 cm, a width of about 8.5 cm, and a height of about 0.58 cm. Although there is no general relative restriction on either the shape or size of the culture chamber, in a preferred embodiment for culturing to achieve a high density of cells, the average distance between the two membranes is in a range of from about 0.05 to about 0.4 inches, and more preferably is in the range of from about 0.07 to about 0.08 inches.

Examples of transparent heaters are well known in the art, and are commercially available. Generally, a transparent heater comprises a very thin (so as to minimize visual interference) conductive layer formed on a transparent substrate. In a preferred embodiment, the transparent substrate, and hence the transparent heater, is gas-permeable. For example, electrodes may be formed by coating (e.g., by etching, chemical means, mechanical means or imprinting) suitable portions of a transparent film (transparent substrate) with a very thin conductive material. In another example, the transparent heater may comprise a laminate, wherein a metallic conductive material is held in position between two transparent polymer sheets (e.g., plastic sheets such as polyethylene). The very thin conductive material may comprise a semiconductor thin layer (e.g., indium tin oxide, indium zinc oxide, generally in a range of from about 1 to 100 nm), a metallic thin layer (e.g., gold, copper, aluminum, and conductive alloys thereof), or a laminate of metallic thin layers (e.g., metallic oxides, metallic nitrides, metallic oxynitrides, metallic carbides, and the like). In a preferred embodiment, and as illustrated in FIG. 1, transparent heater 28 comprises a very thin conductive material 31 comprising a fine resistive wire which minimizes visual interference (e.g., with a diameter of from about 0.01 to about 0.05 mm) which is sandwiched between two films 33 of optical grade polyester (e.g., a total thickness of from about 0.10 mm to about 0.25 mm), in providing a transparency of at least 80% light transmission over the visible spectrum. In a preferred embodiment, transparent heater 28 further a lead attachment area 35, in which insulated lead wires 37 are secured in electrical contact with the conductive material 31, which is spaced apart from the edge of transparent heater 28 (e.g., see FIG.1). This construction may better facilitate assembly of the transparent heater. However, as apparent to one skilled in the art, other constructions are available (e.g., tab extending from transparent heater comprises the lead attachment area).

Figure 2:
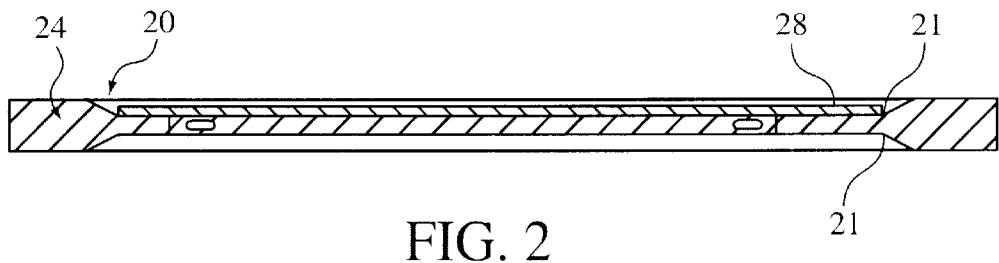
FIG. 2 is a cross-sectional view, taken lengthwise, of an embodiment of the controlled heater device according to the present invention.
Figure 3:
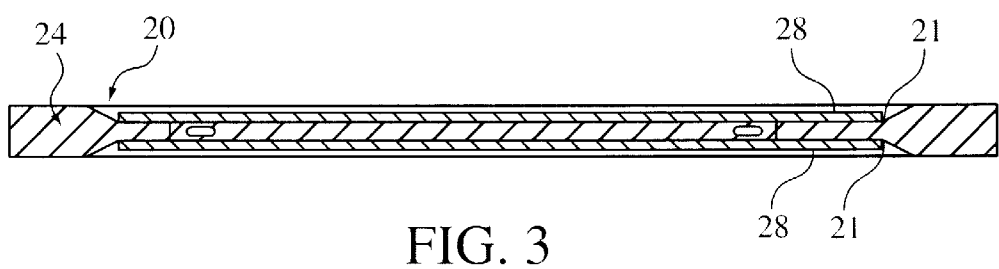
FIG. 3 is a cross-sectional view, taken lengthwise, of an embodiment of the controlled heater device according to the present invention.
Figure 4:
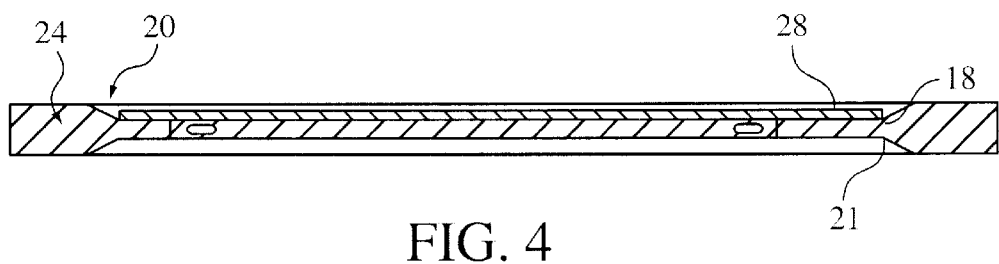
FIG. 4 is a cross-sectional view, taken lengthwise, of an embodiment of the controlled heater device according to the present invention.
Figure 5:
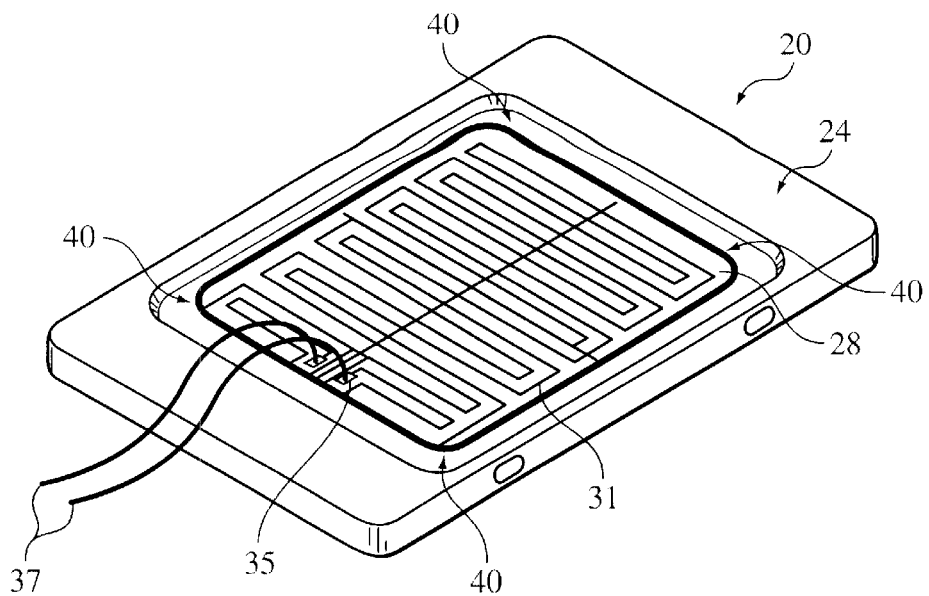
FIG. 5 is a perspective view of another embodiment of the controlled heater device according to the present invention.

In assembling controlled heater device 20, at least one transparent heater 28 is in thermal contact with cell culture apparatus in a manner that transparent heater 28 uniformly heats the contents of culture chamber 40 (e.g., cells cultured therein). In referring to FIG. 2, in a preferred embodiment a transparent heater 28 is in direct thermal contact with an optical surface (e.g., a transparent membrane or a rigid (plastic or glass), transparent surface) of cell culture apparatus 24 in forming controlled heater device 20. In referring to FIG. 3, in another embodiment each of two transparent heaters 28 is in direct thermal contact with a respective, opposing, optical surface of cell culture apparatus 24 in forming controlled heater device 20. Transparent heater 28 may be secured to membrane 21 by a means that may include mechanical means, chemical means (an adhesive agent which may include, but is not limited to, a pressure-sensitive acrylic adhesive, hot-melt adhesive, rubber cement, or any other form of adhesive or bonding agent useful for the purposes attendant to the present invention), or other suitable means (e.g., heat bonding). In a preferred embodiment, transparent heater 28 is bonded to membrane 21 using a transparent pressure-sensitive adhesive. Transparent pressure-sensitive adhesives are well known in the art, and may include, but are not limited to, acrylic adhesives, and cyanoacrylate reactive adhesives. In referring to FIG. 4, in another embodiment, transparent heater 28 is directly secured to frame 18, in a leak-proof sealing, using means that may include mechanical means, chemical means (an adhesive agent which may include, but is not limited to, a pressure-sensitive acrylic adhesive, hot-melt adhesive, rubber cement, or any other form of adhesive or bonding agent useful for the purposes attendant to the present invention), or other suitable means. Other suitable means may include one or more of heat bonding, sonic welding, pressure fit sealing in forming a leak-proof seal, and a molding process in which the transparent heater becomes an integral part of the frame (e.g., by extrusion). In a preferred embodiment, the transparent heater is secured to the frame by a sonic welding process which comprises cutting the frame and bonding (melting) the transparent heater to substantially the cut portion of the frame in a manner which results in a leak-proof sealing between the transparent heater and an opposing optical surface (e.g., a membrane) secured to the frame in the formation of a culture chamber, in a process of assembling the controlled heater device according to the present invention. Whether the transparent heater is secured to a membrane or to the frame of cell culture apparatus 24 in forming controlled heater device 20, as illustrated in FIG. 5, heated are cells that may be cultured in multiple culture chambers 40 of the cell culture apparatus.

Figure 6:
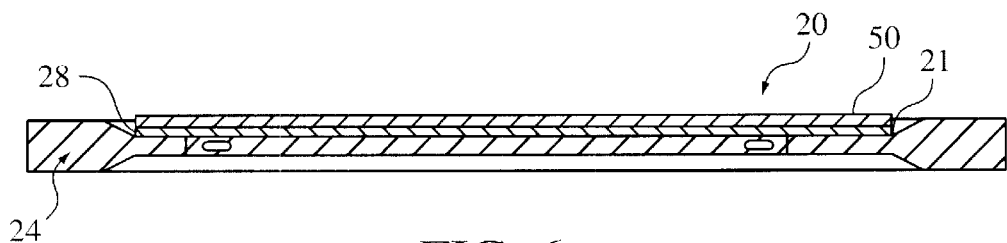
FIG. 6 is a cross-sectional view, taken lengthwise, of an embodiment of the controlled heater device according to the present invention.
Figure 7:
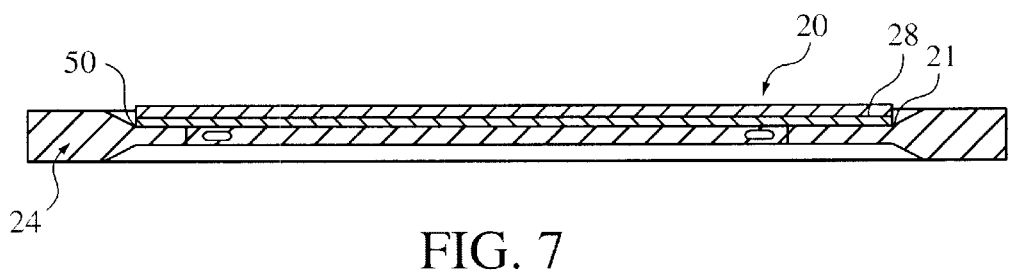
FIG. 7 is a cross-sectional view, taken lengthwise, of an embodiment of the controlled heater device according to the present invention.
Figure 8:
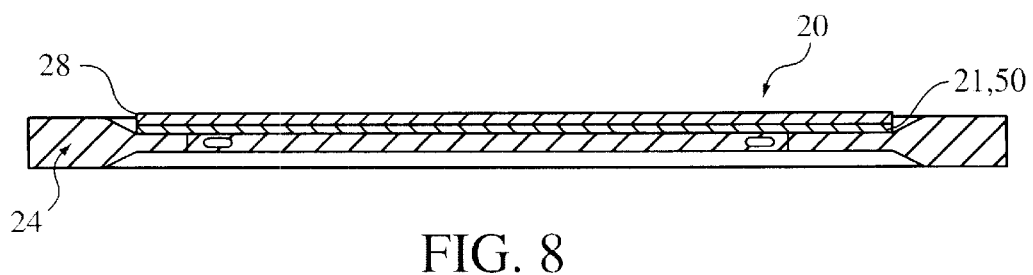
FIG. 8 is a cross-sectional view, taken lengthwise, of an embodiment of the controlled heater device according to the present invention.
Figure 9:
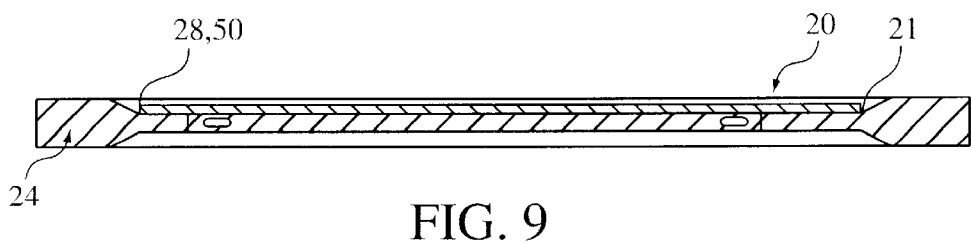
FIG. 9 is a cross-sectional view, taken lengthwise, of an embodiment of the controlled heater device according to the present invention.

Referring to FIG. 6, controlled heater device 20, for heating cultured cells, comprises cell culture apparatus 24 which provides optimal gas transfer through one or more of its surfaces, at least one transparent heater 28 which is in thermal contact with cell culture apparatus 24, and further comprises transparent filter 50. Transparent filter 50 is provided, in an optical path with respect to the cells cultured in the controlled heater device, to prevent a predetermined light spectral range from passing through the transparent filter. For example, if it is desired to expose the cells to UV light, a transparent filter which allows passage of UV light therethrough, but which substantially prevents passage of light in the visible spectrum, may be used. In another illustrative example, the transparent filter may prevent light in a spectral range of from about 550 nm to about 700 nm from passing therethrough, but allows visible light having a spectral range outside from about 550 nm to about 700 nm to pass through. In a preferred embodiment of this latter example, the color of the transparent filter is a color selected from the color range of blue to blue green to a dark green. As apparent to one skilled in the art, other colors may be selected for the transparent filter, depending on what predetermined spectral range of light is desired to be passed therethrough. In one embodiment, the transparent filter comprises a transparent polymer sheet or film which is colored with a pigment so as filter out the desired spectral range of light. In a preferred embodiment, the transparent filter is gas-permeable. A suitable polymer sheet or film may include, but is not limited to, polystyrene, polyethylene, polycarbonate, polyolefin, ethylene vinyl acetate, polypropylene, polysulfone, and the like. In this embodiment, the transparent filter 50 is preferably placed over (on top of) and in contact with transparent heater 28 in forming controlled heater device 20, as illustrated in FIG. 6. In an alternative embodiment, as illustrated in FIG. 7, the transparent filter may be disposed between transparent heater 28 and cell culture apparatus 24 in forming controlled heater device 20 (e.g., sandwiched between the transparent heater and the membrane surface of the cell culture apparatus). In either of these embodiments, the transparent filter may be secured to the transparent heater 28 or to membrane 21 or to frame 18, or a combination thereof, using means that may include mechanical means, chemical means (an adhesive agent which may include, but is not limited to, a pressure sensitive acrylic adhesive, hot-melt adhesive, rubber cement, or any other form of adhesive or bonding agent useful for the purposes attendant to the present invention), or other suitable means. In another embodiment, as illustrated in FIG. 8, membrane 21 may comprise transparent filter 50 (e.g., a gas permeable membrane is pigmented), wherein membrane 21 is secured, in a leak-proof sealing to frame 18. In yet another embodiment, as illustrated in FIG. 9, transparent heater 28 may further comprise transparent filter 50 (e.g., is laminated as a part of transparent heater 28, or a pigment is added to the transparent substrate of transparent heater 28). In a further embodiment, transparent heater 28 comprises transparent filter 50 and a transparent, liquid impermeable membrane, and may be secured in a leak-proof sealing to the frame of the cell culture apparatus using means as previously described herein. In that regard, the transparent heater may comprise a transparent substrate that is pigmented so as to function as the transparent filter, and further, is treated on a surface (the surface which is secured to the cell culture apparatus in forming a controlled heater device) to promote adhesion of anchorage-dependent cells that come in contact with the treated surface. As previously described in more detail herein, the treatment may comprise ionization of the surface. In a example for illustrative purposes only, the transparent heater may comprise a laminate wherein a metallic conductive material is held in position between two transparent polymer sheets, wherein one of the polymer sheets may be pigmented so as to function as the transparent filter, and one of the polymer sheets is treated to promote adhesion of anchorage-dependent cells that come in contact with the treated surface. In a preferred embodiment, the transparent heater, comprising the transparent filter and a membrane treated to promote adhesion of anchorage-dependent cells, is gas-permeable.

Figure 10:
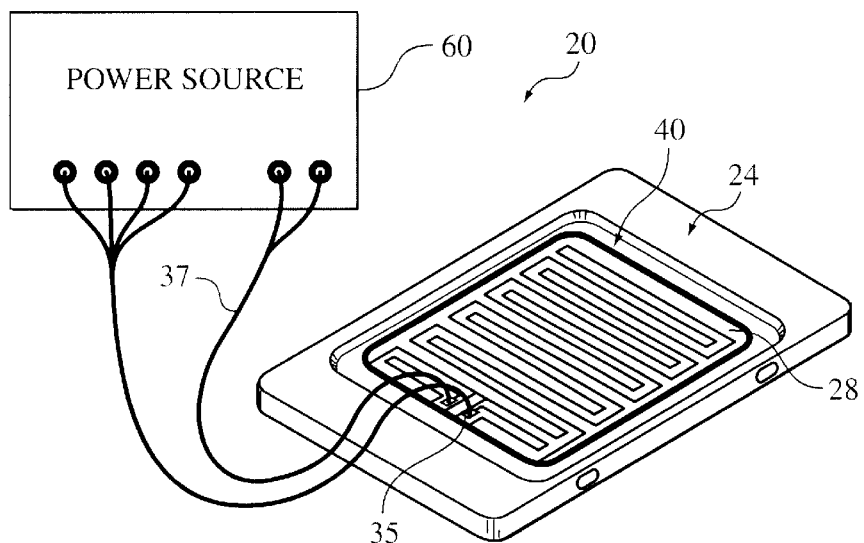
FIG. 10 is a perspective view of an embodiment of the controlled heater device according to the present invention.

Referring to FIG. 10, controlled heater device 20, adapted to heat cultured cells, comprises cell culture apparatus 24 which provides optimal gas transfer through one or more of its surfaces, at least one transparent heater 28 in thermal contact with cell culture apparatus 24, and further comprises a power source 60 for supplying electric power to transparent heater 28 of controlled heater device 20. In an alternative embodiment, and referring to FIG. 11, controlled heater device 20, adapted to heat cultured cells, comprises cell culture apparatus 24 which provides optimal gas transfer through one or more of its surfaces, at least one transparent heater 28 in thermal contact with cell culture apparatus 24, transparent filter 50, and further comprises a power source 60 for supplying electric power to transparent heater 28 of controlled heater device 20. Power source 60 may comprise a power supply or a temperature controller. When a power supply is used, the power supply supplies a constant current that has been predetermined to heat transparent heater 28 of controlled heater device 20 to a predetermined temperature. The power source may comprise a temperature controller comprising a temperature sensor and a current controller that controls the supply of current to transparent heater 28 of controlled heater device 20. Power supplies and temperature controllers are well known in the art. A temperature controller receives a signal from the temperature sensor to sense the present temperature of the controlled heater device (e.g., of the transparent heater 28 or of the contents in the culture chamber of the cell culture apparatus), and to control the amount of heat generated by transparent heater 28. If the sensed temperature is not within a predetermined temperature range, the temperature controller alters the voltage to adjust the temperature generated by the transparent heater to within the predetermined temperature range (e.g., increase in voltage to increase temperature if temperature is below the predetermined temperature range, or decrease in voltage to decrease temperature if temperature is above the predetermined temperature range). The temperature sensor may comprise a resistance thermometer (e.g., platinum wire) or thermometer that is incorporated into the transparent heater (e.g., wound separately from the conductive layer) in sensing the temperature of the transparent heater, or inserted into the cell culture chamber (e.g., into or through an aperture of the cell culture apparatus) of the controlled heater device to sense the temperature of the culture chamber contents (e.g., cell culture medium and/or cultured cells) of the controlled heater device.

In a preferred embodiment, an optical surface of the controlled heater device 20 comprises thin grid lines 42 formed thereon or formed as a part thereof. The optical surface is selected from the group consisting of the transparent heater, a transparent membrane, a transparent rigid plastic surface, transparent filter, and a combination thereof. Preferably, the grid lines are on an optical surface that serves as the surface of the controlled heated device on which anchorage-dependent cells are attached. The grid lines are thin so as to minimize visual interference, but provide coordinate means for locating a specific cell or groups of cultured cells. Coordinate means facilitates time-lapse video-recording, and particularly scanning time-lapse video-recording.

EXAMPLE 1

Figure 11:
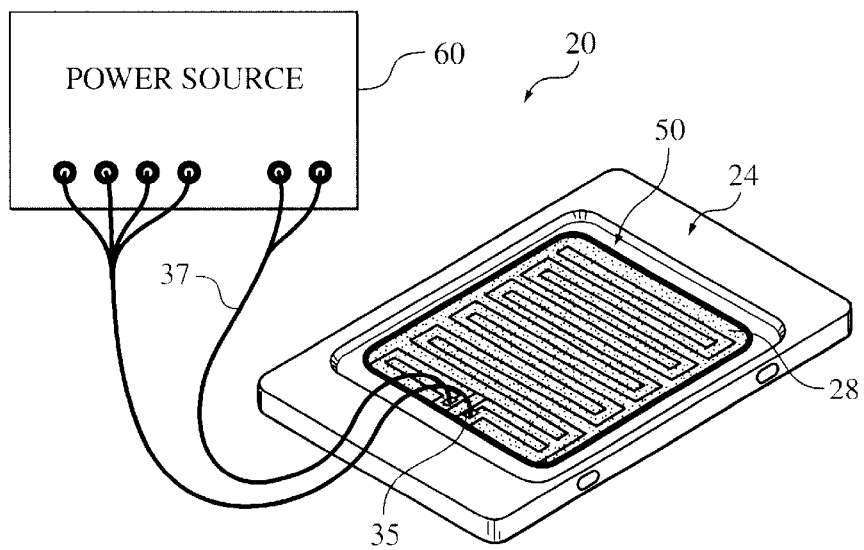
FIG. 11 is a perspective view of an embodiment of the controlled heater device according to the present invention.

This example illustrates use of the controlled heater device according to the present invention. T47-D cells, a human breast carcinoma cell line, were introduced into the controlled heater device (as illustrated in FIG. 11). The controlled heater further comprised a power source that controlled the temperature of the cultured cells to a desired temperature of about 37° C. The controlled heater device was placed onto a microscope stage of a phase contrast microscope. The microscope was operatively connected to a ccd camera that was operatively connected to a computer. Using this arrangement, a field of cells was selected and viewed under a 20× objective lens for time-lapse video-recording during which images were recorded every 30 seconds during three 12 hour periods over 3 days. Over the 3 day period, the cultured cells grew exponentially, and cell movement and growth was recorded.

The foregoing description of the specific embodiments of the present invention have been described in detail for purposes of illustration. In view of the descriptions and illustrations, others skilled in the art can, by applying, current knowledge, readily modify and/or adapt the present invention for various applications without departing from the basic concept, and therefore such modifications and/or adaptations are intended to be within the meaning and scope of the appended claims.

What is claimed:

1. A controlled heater device for heating cultured cells, the controlled heater device comprising:
   a cell culture apparatus comprising at least one gas permeable, liquid impermeable membrane; and
   at least one transparent heater in thermal contact with the cell culture apparatus.

2. The controlled heater device according to claim 1, wherein the controlled heater device provides an optical path that enables imaging of cells cultured in the controlled heater device.

3. The controlled heater device according to claim 1, wherein the at least one transparent heater is a transparent heater that comprises a laminate comprised of a metallic conductive material held in position between two transparent polymer sheets.

4. The controlled heater device according to claim 3, wherein the transparent heater further comprises a lead attachment area in which insulated lead wires are secured in electrical contact with the conductive material.

5. The controlled heater device according to claim 1, wherein the transparent heater is secured to a transparent, gas permeable, liquid impermeable membrane of the cell culture apparatus in forming the controlled heater device.

6. The controlled heater device according to claim 1, wherein the transparent heater is secured, in a leak-proof sealing, to a frame of the cell culture apparatus in forming the controlled heater device.

7. The controlled heater device according to claim 1, wherein the cell culture apparatus comprises multiple culture chambers.

8. The controlled heater device according to claim 1, further comprising a power source, a transparent filter, and a combination thereof.

9. The controlled heater device according to claim 8, wherein the controlled heater device further comprises a transparent filter provided in an optical path with respect to cells cultured in the controlled heater device, wherein the transparent filter prevents a predetermined spectral range of light from passing through the transparent filter.

10. The controlled heater device according to claim 9, wherein the predetermined spectral range of light is in a spectral range of from about 550 nm to about 700 nm.

11. The controlled heater device according to claim 9, wherein the transparent filter is gas-permeable.

12. The controlled heater device according to claim 9, wherein the transparent filter is secured to a surface selected from the group consisting of the transparent filter, the transparent, gas-permeable membrane, a frame of the cell culture apparatus, and a combination thereof.

13. The controlled heater device according to claim 9, wherein the transparent, gas-permeable membrane comprises the transparent filter.

14. The controlled heater device according to claim 9, wherein the transparent heater comprises the transparent filter.

15. The controlled heater device according to claim 9, wherein the transparent heater comprises the transparent filter and the transparent, gas-permeable membrane.

16. The controlled heater device according to claim 9, wherein the controlled heater device further comprises a power source for controlling the amount of heat generated by the transparent heater of the controlled heater device.

17. The controlled heater device according to claim 9, wherein the power source further comprises a temperature sensor.

18. The controlled heater device according to claim 17, wherein the temperature sensor senses the temperature of the transparent heater of the controlled heater device.

19. The controlled heater device according to claim 17, wherein the temperature sensor senses the temperature of contents in a culture chamber of the controlled heater device.

20. The controlled heater device according to claim 1, further comprising grid lines on an optical surface of the controlled heater device.

21. A controlled heater device for heating cultured cells, the controlled heater device comprising:
  a cell culture apparatus comprising at least one transparent, gas permeable, liquid impermeable membrane;
  a transparent heater in thermal contact with the cell culture apparatus; and
  a transparent filter provided to prevent a predetermined spectral range of light from passing through the transparent filter;
wherein the transparent membrane, transparent heater, and transparent filter comprise optical surfaces that are aligned with respect to each other so as to provide an optical path that enables imaging of cells culture in the controlled heater device.

22. The controlled heater device according to claim 21, wherein the controlled heater device further comprises a power source for controlling the amount of heat generated by the transparent heater of the controlled heater device.

23. The controlled heater device according to claim 22, wherein the power source further comprises a temperature sensor for sensing the temperature of an object selected from the group consisting of the transparent heater, and contents in a culture chamber of the controlled heater device.

24. The controlled heater device according to claim 21, wherein the controlled heater device further comprises grid lines on an optical surface of the controlled heater device.

25. A transparent heater comprising a transparent filter and a transparent liquid impermeable membrane, wherein the transparent filter is adapted to prevent a predetermined light spectral range from passing therethrough, and wherein the membrane is treated on a surface to promote adhesion of anchorage-dependent cells that come in contact with the treated surface.

26. The transparent heater according to claim 25, wherein the transparent heater further comprises a lead attachment area in which insulated lead wires are secured in electrical contact with conductive material of the transparent heater.

27. The transparent heater according to claim 25, wherein the transparent heater is gas permeable.

* * * * *